United States Patent [19]

Lorenz et al.

[11] 4,355,019

[45] Oct. 19, 1982

[54] HEPATITIS A TESTING AND GROWTH IN TREE SHREW AS ANIMAL MODEL

[75] Inventors: Peter Lorenz, Frankfurt am Main; Anita Schwaier, Eschborn, both of Fed. Rep. of Germany

[73] Assignee: Battelle-Institut e.V., Frankfurt am Main, Fed. Rep. of Germany

[21] Appl. No.: 182,490

[22] Filed: Aug. 29, 1980

[30] Foreign Application Priority Data

Sep. 4, 1979 [DE]  Fed. Rep. of Germany ....... 2935634

[51] Int. Cl.$^3$ ..................... A61K 39/29; A61K 47/00; C12Q 1/18; C12Q 1/22; C12Q 1/70; G01N 33/54

[52] U.S. Cl. ......................................... 424/9; 424/86; 424/89; 435/5; 435/31; 435/32

[58] Field of Search ................... 424/9, 85, 86, 88, 89; 435/5, 30, 31, 32

[56] References Cited

U.S. PATENT DOCUMENTS

3,105,011  9/1963  McLean, Jr. .......................... 167/78
4,017,360  4/1977  Bertland et al. ...................... 424/89

FOREIGN PATENT DOCUMENTS

2621276  6/1972  Fed. Rep. of Germany .

OTHER PUBLICATIONS

Mitruka, Animals for Med. Res. John Wiley & Sons, New York 1976, pp. 162, 163, 523, 560, 573, 574.
Mitruka et al., Animals for Med. Res., John Wiley & Sons, NY 1976, p. 561.
Litterst, Chem. Abs. vol. 85, 1976 Ab. No. 85:28465j.
Provost, PSEBM, vol. 142, 1973 pp. 1257-1267.
Blumborg, CRC Critical Reviews in Clin. Lab. Sci., The Chem. Rubber Co. 1971, pp. 493, 490-497.
Lennette, Manual of Clin. Microbiol., ASM, Wash. DC 2nd Ed, 1974 p. 837.
The New Encyclopedia Britannica, Macropaedia, 1974 vol. 19 pp. 170, 171; vol. 14; vol. 9; vol. X.
The Washington Post, Feb. 20, 1982 p. A10.
Dolbecco et al. (Ed), Microbiology, Handbook, 1981, pp. 855-857, 863, 879.
Chemical Abstracts, vol. 75, (1971), 3202b.
Chemical Abstracts, vol. 82 (1975) 14910B.
Das, P. C., et al. "A Method for Production of Antibody to Hepatitis-Associated Antigen In Rabbits", British Journal Haematology, vol. 20, (1971) pp. 363 to 367.
Booth, J. R. et al., "Separation of Hepatitis-Associates Antigen" (HAA), Vox Sang., vol. 27, (1974) pp. 227 to 231.
Schwaier, Anita, "The Breeding Stock Of Tupaias At The Battelle-Institut", Laboratory Animal Handbooks, vol. 6, (1975), pp. 141 to 149.
Kuhn, Hans-Jurg, et al., "Implantation, Early Placentation, And The Chronology Of Embryogenesis In Tupaia belangeri", Z. Anat. Entwickl.-Gesch., vol. 142 (1973), pp. 315 to 340.
Schwaier, Anita, "Tupaias-eine neue Versuchstierart fuer die medizinische Forschung", Umschau 77 (13), (1977), pp. 447 to 449.
Schwaier, Anita, "Method Of Blood Sampling And Intraveneous Injection" In Tapaias (Tree Shrews), Versuchstierk., vol. 16, (1974), pp. 35 to 39.
Schwaier, Anita, "Tupaias-Low-Cost Primates For Medical Research".
Gordon et al., Primate Utilization And Conservation (1975), pp. 141 to 150.
Darai, G. et al., "Experimental Infection of *Tupaia belangeri* (Tree Shrews) with Herpes Simplex Virus Types 1 and 2", Journal of Infectious Diseases, vol. 137, No. 3 (Mar. 1978), pp. 221 to 226.

*Primary Examiner*—Anna P. Fagelson
*Attorney, Agent, or Firm*—Fisher, Christen & Sabol

[57] ABSTRACT

Tree shrews (*Tupaia belangeri*) are used as an animal model to test the inactivation of vaccines, the harmlessness of blood products and the effectiveness of chemotherapeutic agents and disinfectants against viral hepatitis. The antibody determinations are performed at specific intervals for a period of 150 days in the case of viral hepatitis type A and 60 days in the case of viral hepatitis type B.

16 Claims, No Drawings

HEPATITIS A TESTING AND GROWTH IN TREE SHREW AS ANIMAL MODEL

BACKGROUND OF THIS INVENTION

1. Field of this Invention

This invention relates to a process for testing for the inactivation of vaccines, harmlessness of blood products and effectiveness of chemotherapeutic agents and disinfectants against viral hepatitis, in particular type A and type B, by the determination of antibodies in the animal model. It further relates to a process for the growth and collection of viral hepatitis antigen, particularly type A and type B, from the animal model.

2. Prior Art

In the activation of vaccines, the vaccine is deprived of its power to multiply, while the pathogens retain their antigenicity and thus retain the ability to immunize the vaccinated person. Testing for inactivation is of great importance both with respect to the effectiveness and harmlessness or toxicity of the vaccine. Furthermore, products made from donated blood, e.g., coagulation factors, albumins and globulins, are administered to patients to cure various diseases or as a treatment for circulation problems. To ensure that these materials do not contain any hepatitis viruses, they must first be examined using a suitable animal model. The effectiveness of chemotherapeutic agents, which is decisive for the number and size of doses to be administered and thus in turn affects the patient's tolerance of the preparation, is just as important as the harmlessness of vaccines and blood products.

Disinfectants must be available for work in laboratories, hospitals, etc., in order to be able to destroy any infectious material that might be present. Disinfectant solutions containing formalin are currently used against viral hepatitis, but they have the disadvantage of having a strong smell, and in the case of prolonged action, they involve the possibility of carcinogenesis. Animal models are also necessary to test the effectiveness of new developments in this field.

Currently known animal models for viral hepatitis type A include marmosets and anthropoids of the types S. mystax, S. nigricollis, S. fuscicollis, S. oedipus, *Callithrix jacchus,* C. argentata, *Cercopithecus aethiops,* Pantroglodytes and *Anthropopithecus troglodytes.* For viral hepatitis type B, primates, e.g., chimpanzees, are the only known animal model. All these animal models are too expensive to maintain and some of them are threatened with extinction. In addition, breeding is uneconomic because for example in the case of C. jacchus only four offspring per breeding pair per year at most can be bred. Other more readily available subprimates or primates are not known as animal models for hepatitis viruses.

BROAD DESCRIPTION OF THIS INVENTION

The main object of this invention is, therefore, to create a reliable and economical method of testing vaccines, blood products, chemotherapeutic agents and disinfectants that does not have the disadvantages referred to above. An animal model had to be found that it is suitable for the multiplication of hepatitis viruses.

It has been found that the main object of this invention is achieved by performing the antibody determinations on tree shrews (*Tupaia belangeri*). For the multiplication and collection of hepatitis virus antigen, tree shrews are infected with hepatitis viruses, and the antigen is collected in the known way from organs and excretions of the infected animals or from cell cultures which are made from the organs of the animals. In this way a starting product for vaccines against hepatitis pathogens can be obtained.

In the testing of vaccines, blood products, chemotherapeutic agents and disinfectants, the tree shrews are examined for the formation of the specific antibodies. In the case of viral hepatitis type A, the antibody determinations are performed for 150 days, preferably at weekly intervals. In the case of viral hepatitis type B, the antibody determinations are performed for a period of 60 days, beginning on the fourth day after infection at the latest, twice during the first week and then once a week. The examination is for the formation of antibodies against the surface antigen (HBsAg; Anti-HBs) and against the core antigen (HBcAg; Anti-HBc). The progress of the infection is promoted by an immunosuppressive treatment, e.g., by intramuscular vaccination with Hostacortin (5 mg/kg) and Endoxan (10 mg/kg) on alternate days, beginning three days before infection and continuing until the seventh day after infection, so that antibodies against HBcAg can be identified just two weeks after injection.

Tree shrews are phyletically advanced and belong to the subprimates. They have advantages over apes, particularly with respect to breeding. One tree shrew breeding pair can produce up to 20 offspring per year. It has been found that the animals react to the intravenous administration of foreign proteins or antigens by the formation of specific antibodies capable of being identified just four days later. This immediate immune response occurs with hepatitis virus type B and is characteristic of the formation of antibodies against the surface antigen of the viruses (HBsAg). The formation of antibodies against the core antigen (HBcAg) on the other hand only occurs after a delay of at least 16 days. The reaction to the HBsAg represents a rapid immune response to a foreign protein in the form of an active immunization with a killed vaccine. The time lag in the reaction to HBcAg, however, indicates that the antigen has multiplied inside the experimental animal before it could cause the formation of antibodies. The detection of the anti-HBcAg antibody is thus proof of the infectiousness of the vaccine or blood product under investigation. If the animals are infected with viral hepatitis type A, the immune response also occurs only after a time lag, thus indicating a multiplication of the pathogen in this species.

In the testing of substances for their antiviral effect against hepatitis viruses, chemotherapeutic agents are administered to the infected animals and antibody determinations are performed according to the known techniques.

For the safety testing of disinfectants, a specific quantity of infectious virus particles is added to the disinfectants in various concentrations under various conditions, such as various temperatures and times, and the virus particles are finally centrifuged out of the suspension, resuspended in a physiological buffer and vaccinated into the animal. If the animal contracts viral hepatitis, the pathogens have not been killed by treatment with the disinfectant solution. This means that the disinfectant is not suitable for the inactivation of the hepatitis viruses.

Other objects and advantages of this invention are set out herein or are obvious herefrom to one ordinarily skilled in the art. The objects and advantages of this invention are achieved by the processes of this invention.

DETAILED DESCRIPTION OF THIS INVENTION

This invention is described in greater detail by the following examples:

EXAMPLE 1

Four tree shrews are each given intravenous injections of 0.5 ml of a suspension of hepatitis viruses type B, which had first been purified by sucrose gradient centrifugation and diluted in chimpanzee plasma and finally with 1.5 volumes of a salt solution according to Hanks. Two animals are given immunosuppressive treatments according to the method described above. Serum samples are taken from the fourth day after infection and the seventh day after infection at weekly intervals and are examined for the content of antibodies against HBcAg and HBsAg. In all four animals antibodies against HBsAg can be identified as early as the fourth day after infection. In the animals that were not given the immunosuppressive treatment, however, antibodies against HBcAg are not detected until the 20th and 42nd day after infection. After infection under immunosuppression, antibodies against HBcAg can be detected just 14 days after infection. The pathohistological examination after completion of the experiments revealed the typical damage to the livers of the experimental animals.

EXAMPLE 2

Two tree shrews are infected intravenously with hepatitis virus type A. Then, from the fourth day after infection, weekly serum samples are examined for the formation of specific antibodies. In contrast to the rapid immune response after vaccination with hepatitis virus type B, small quantities of antibodies against hepatitis virus type A can only be detected 35 and 42 days after infection. The results show that the formation of antibodies increases until the 150th day after infection. On the 91st day after infection the animals are found to have slightly elevated serum transaminase values (SGOT or SGOT and SGPT), indicating damage to the liver as a result of infection. The delayed immune response and the elevated serum transaminase values imply that the tree shrew is a suitable animal model for testing the effectiveness of substances to combat viral hepatitis type A. The pathohistological examination performed on completion of the experiment shows—as stated in Example 1—that the livers of the experimental animals were damaged in the typical manner.

What is claimed is:

1. Process for the growth and collection of viral hepatitis antigen type A from a tree shrew (*Tupaia belangeri*), which is used as an animal model, comprising:
   (a) infecting said tree shrew with viral hepatitis type A;
   (b) performing at least one antibody determination at specific intervals over a period of about 150 days after infection of said tree shrew; and
   (c) obtaining said viral hepatitis antigen type A from said infected tree shrew.

2. Process as claimed in claim 1 wherein the immune defense of said tree shrew has previously been suppressed by adequate therapy.

3. Process as claimed in claim 2 wherein said antibody determinations are conducted at weekly intervals over a period of 150 days after infection of said tree shrew.

4. Process as claimed in claim 2 wherein said viral hepatitis antigen type A is obtained from an organ or organs or excretion or a mixture thereof of the infected tree shrew.

5. Process as claimed in claim 2 wherein said viral hepatitis antigen type A is obtained from one or more cell cultures made from an organ or organs or excretion or mixture thereof of the infected tree shrew.

6. Process for testing the effectiveness of a disinfectant against viral hepatities type A comprising:
   (a) admixing a specific quantity of said viral hepatitis type A to form a suspension;
   (b) removing said viral hepatitis type A from said suspension;
   (c) admixing said viral hepatitis type A from step (b) with a physiological buffer to form a suspension;
   (d) vaccinating a tree shrew (*Tupaia belangeri*), which is used as an animal model, with the suspension from step (c); and
   (e) performing at least one antibody determination at specific intervals over a period of about 150 days after infection of said tree shrew, whereby said disinfectant is determined to be effective or ineffective against said viral hepatitis type A if said tree shrew, respectively, does not contract viral hepatitis or does contract viral hepatitis.

7. Process as claimed in claim 6 wherein said removal step (b) is achieved by means of centrifugation.

8. Process as claimed in claim 7 wherein said antibody determinations are conducted at weekly intervals over a period of 150 days after infection of said tree shrew.

9. Process for testing the antiviral effectiveness of a chemotherapeutic agent against viral hepatitis type A comprising:
   (a) infecting a tree shrew (*Tupaia belangeri*), which is used as an animal model,
   (b) administering said chemotherapeutic agent to said infected tree shrew; and
   (c) performing at least one antibody determination at specific intervals over a period of about 150 days after infection of said tree shrew,
   whereby said chemotherapeutic agent is determined to be ineffective against said viral hepatitis type A if said antibody determination detects HAAg antibody in said tree shrew.

10. Process as claimed in claim 9 wherein said antibody determinations are conducted at weekly intervals over a period of 150 days after infection of said tree shrew.

11. Process for testing for the absence of viral hepatitis type A in blood products comprising:
    (a) administering said blood product to a tree shrew (*Tupaia belangeri*), which is used as an animal model, with viral hepatitis type A; and
    (b) performing at least one antibody determination at specific intervals over a period of about 150 days after infection of said tree shrew,
    whereby said blood product is determined to contain said viral hepatitis type A if said antibody determination detects HAAg antibody in said tree shrew.

12. Process as claimed in claim 11 wherein said antibody determinations are conducted at weekly intervals over a period of 150 days after infection of said tree shrew.

13. Process as claimed in claim 11 wherein said blood product was intraveneously administered to said tree shrew.

14. Process for testing the antiviral ineffectiveness of a vaccine against viral hepatitis type A comprising:
    (a) infecting a tree shrew (*Tupaia belangeri*), which is used as an animal model, with viral hepatitis type A;
    (b) administering said vaccine to said infected tree shrew; and
    (c) performing at least one antibody determination at specific intervals over a period of about 150 days after infection of said tree shrew, whereby said vaccine is determined to be ineffective against said viral hepatitis type A if said antibody determination detects HAAg antibody in said tree shrew.

15. Process as claimed in claim 14 wherein said antibody determinations are conducted at weekly intervals over a period of 150 days after infection of said tree shrew.

16. Process as claimed in claim 14 wherein said vaccine was intraveneously administered to said tree shrew.

* * * * *